United States Patent
Ryan et al.

(10) Patent No.: US 10,682,306 B1
(45) Date of Patent: Jun. 16, 2020

(54) COMPOSITIONS AND METHODS FOR TREATING SKIN

(71) Applicant: CODEX BEAUTY CORPORATION, Portola Valley, CA (US)

(72) Inventors: Tracey Ryan, Cork (IE); Marc Cornell, Portola Valley, CA (US); Barbara A. Paldus, Portola Valley, CA (US)

(73) Assignee: CODEX BEAUTY CORPORATION, Portola Valley, CA (US)

( * ) Notice: Subject to any disclaimer, the term of this patent is extended or adjusted under 35 U.S.C. 154(b) by 0 days.

(21) Appl. No.: 16/669,098

(22) Filed: Oct. 30, 2019

Related U.S. Application Data

(60) Provisional application No. 62/853,116, filed on May 27, 2019, provisional application No. 62/853,588, filed on May 28, 2019, provisional application No. 62/861,745, filed on Jun. 14, 2019.

(51) Int. Cl.
| | | |
|---|---|---|
| *A61K 8/9789* | (2017.01) | |
| *A61Q 19/00* | (2006.01) | |
| *A61K 8/92* | (2006.01) | |

(52) U.S. Cl.
CPC ............ *A61K 8/9789* (2017.08); *A61K 8/922* (2013.01); *A61Q 19/007* (2013.01)

(58) Field of Classification Search
CPC .................................................. A61K 8/9789
See application file for complete search history.

(56) References Cited

U.S. PATENT DOCUMENTS

| | | |
|---|---|---|
| 4,933,177 A | 6/1990 | Grollier et al. |
| 7,678,768 B2 | 3/2010 | Purpura et al. |
| 2017/0252293 A1* | 9/2017 | Brumbaugh ......... A61Q 19/007 |

FOREIGN PATENT DOCUMENTS

| | | |
|---|---|---|
| GB | 2485483 A | 5/2012 |
| WO | 2006032091 A2 | 3/2006 |
| WO | 2012033422 A1 | 3/2012 |
| WO | 2013149323 A1 | 10/2013 |
| WO | 2015175333 A1 | 11/2015 |
| WO | 2019002714 A1 | 1/2019 |

OTHER PUBLICATIONS

English bibliographic information for Orescanin, HR 2016001267 A2, a Croatian published patent application, 2018.*
English bibliographic information for Institutul de Tehnologie Chimica, RO 120529 B1, a Rumanian patent, 2006.*
Inhaltsstoffe Kosmetika et al., "S KW", Inhaltsstoffe Kosmetika, Dec. 31, 2005, 274 Pages.
International Search Report and Written Opinion from PCT Application No. PCT/US2019/058822, dated Jan. 28, 2020.

\* cited by examiner

*Primary Examiner* — Rosanne Kosson
(74) *Attorney, Agent, or Firm* — Workman Nydegger

(57) ABSTRACT

The present disclosure is directed to a composition and method of enhancing skin health and appearance, as well as treating compromised skin, by applying onto the skin a composition containing a moisturizing/hydrating-effective amount of a mixture of at least: (a) an oil infusion of *Calendula officinalis* extract; (b) an oil infusion of *Helichrysum italicum* extract; (c) an oil infusion of *Symphytum officinale* extract; (d) an aqueous infusion of *Viola tricolor* extract; and (e) an aqueous infusion of at least one *Mallow* extract chosen from *Malva sylvestris* extract and *Althea officinalis* extract; and an emulsifying-effective amount of a dermatologically-acceptable emulsifier, wherein the composition is natural and free of a skin sensitizing-effective amount of an essential oil.

25 Claims, No Drawings

COMPOSITIONS AND METHODS FOR TREATING SKIN

FIELD OF THE INVENTION

The disclosure relates to compositions and methods of enhancing the health and appearance of human skin using botanical ingredients, and more particularly to moisturizing compositions, preservatives therefor, and methods of using the same.

BACKGROUND

Skin is subjected to numerous extrinsic and intrinsic negative influences that affect its appearance, physical properties and physiological functions. Extrinsic influences include ultraviolet radiation, environmental pollution, extreme temperatures, harsh surfactants, contamination from consumer products, oxidative stress, and mechanical stress caused by, for example, shaving, abrasions, and the like. Intrinsic influences include chronological aging, a person's genetic makeup, skin homogeneity, skin-barrier function, thickness of the skin layer, degradation of the extracellular matrix, the activity level of particular genes, nuclear cell function, and other biological changes, such as scarring, that occur from within the skin. Regardless of the specific cause, these factors result in the development of fine lines and wrinkles, sagging, and loss of elasticity and firmness, which are oftentimes associated with an attendant reduction in the skin's moisture content.

As the body's largest organ, skin holds in fluids and prevents dehydration. Consequently, it is important to the health and appearance of skin to keep it nourished in order to help counteract the damage caused by the above-referenced extrinsic and intrinsic influences. Dry skin is a particularly common disorder that affects both males and females equally, and is particularly prevalent in older individuals and those genetically predisposed to such a condition. People suffering from dry skin complain of flaking, itching, irritation, and an overall dull, rough and lackluster appearance to their skin. Moreover, as a person ages, their skin tends to produce fewer natural oils that aid in preventing moisture from escaping from the skin, and as a result older individuals are more prone to dehydration.

To counteract the negative impact of these extrinsic and intrinsic influences on skin, treatments such as topical therapy, oral therapy, cosmetic procedures and compositions, nutrition and dietary practices, injections, disruptive lifestyle adjustments, and UV therapy have been developed. Unfortunately, these treatments oftentimes suffer from drawbacks associated with skin irritation and/or prolonged recovery periods. Many cosmetic compositions include synthetic, harsh, petroleum-based, and/or carcinogenic or otherwise harmful ingredients as moisturizers or preservatives because of their low cost and/or efficacy.

For example, a moisturizing composition commonly contains emollients, preservatives, fragrances, and emulsifiers to hold the composition's ingredients together. Any or all of these categories of ingredients may contain synthetic and/or petroleum-based ingredients. For example, the emollient which aids in retaining moisture in the skin may be formed from petroleum and/or synthetic alcohols and may form a waterproof barrier on the skin. In some instances, such synthetic emollients are known to cause irritation or harm to the skin, to not soothe or provide necessary nutrients to the skin, and to be ineffective at moisturizing the skin, particularly over time. Synthetic emollients that are excessively occlusive, such that moisture is trapped against the skin, can interfere with normal skin function. Synthetic preservatives such as phenoxyethanol, parabens, formaldehyde donors, and other compounds can cause skin irritation and other serious health issues. Synthetic fragrances may likewise cause skin irritation and may be toxic. Non-plant-based emulsifiers usually comprise petroleum derivatives.

The use of such ingredients—and the deleterious effects associated therewith—has led to a demand for effective, all-natural cosmetic compositions that include ingredients such as moisturizers, preservatives, and other ingredients while omitting synthetic, petroleum-based, harsh, and/or harmful ingredients.

In response to the outstanding need in the industry for products that meet certain thresholds of "natural" and "organic" ingredients, coupled with the lack of official standards for what qualifies as "natural" and "organic," preservative formulation has become a cottage industry with consumers gravitating towards products containing natural extracts, botanicals, or other ingredients derived from natural sources, while avoiding those products having ingredients that are either known to cause or suspected of causing adverse health reactions. Unfortunately, this ad hoc approach and decentralization of acquired knowledge and experience of generating effective preservative formulations has led to a host of ineffective solutions that typically result in diminished shelf-life and usability of associated topical consumer products.

Various third-party certifications have been established in an attempt to bring consistency and reliability to the use of natural and organic preservatives in topical consumer products. For example, ECOCERT® is an organic certification organization based in Europe that conducts inspections in over 80 countries, making it one of the largest organic certification organizations in the world. ECOCERT® primarily certifies food and food products but also certifies cosmetics, detergents, perfumes, and textiles and is a leading certifier of fair-trade food, cosmetics, and textiles.

Another example is the Cosmetic Organic Standard (COSMOS), a Europe-wide private standard that was developed by five charter members: BDIH (Germany), Cosmebio (France), Ecocert Greenlife SAS (France), ICEA (Italy), and Soil Association (Great Britain). They were all combined under AISBL (international non-profit organization based in Brussels), the purpose of which was to set out minimum common requirements, harmonize organic and natural cosmetic certification rules, and lobby institutions in the sector's interests. COSMOS makes use of the principles in the ECOCERT® standard: to promote the use of ingredients from organic farming, use production and manufacturing processes that are environmentally sound and safe for human health, and include and expand the concept of "green chemicals."

The National Organic Program (NOP), a federal regulatory framework in the United States governing organic food, is yet another certification. The core mission of the NOP is to protect the integrity of the United States Department of Agriculture (USDA) organic seal. The seal is used for products adhering to USDA standards that contain at least 95% organic ingredients.

Yet despite the upwelling demand and need for all-natural cosmetic compositions and despite the certification systems pressuring the market to identify systems as such, existing efforts have had difficulty identifying natural cosmetic compositions that omit undesired ingredients without compromising on effective preservation, moisturizing, or other desired features.

The use of botanical extracts on the skin, and existing attempts to provide natural or plant-based moisturizers and other cosmetics, are limited to, on the one hand, highly limited and narrow descriptions of particularized treatments, such as eczema and psoriasis, and, on the other hand, highly generalized descriptions of botanical extracts that lack helpful instructions on how to actually formulate a skin-treatment product that is stable and effective and which omits harmful ingredients. For example, U.S. Pat. No. 4,933,177 to L'Oreal of Paris, France discusses the use of certain botanical ingredients in skincare, but does not teach or suggest the precise association of ingredients, extraction techniques, and solvents to be used, and ingredients to avoid, to provide an efficacious all-natural product capable of enhancing skin health and appearance.

Because of the number of botanical extracts, solvents, and extraction techniques, a prohibitively large number of possible cosmetic compositions can be conceived. But one cannot merely combine a mixture of random botanical extracts, in arbitrary concentrations, using arbitrary extraction techniques and solvents, with any expectation of successfully formulating a product with intended benefits and properties.

Further, when considering the currently available "all natural" skincare compositions, the reproducibility and scientific rigor of any alleged benefits are of particular concern. This challenge is illustrated by the aforementioned "cottage industry" of do-it-yourself ("DIY") cosmeticians that have arisen on the internet, encouraging others to create their own cosmetic formulations having unsubstantiated benefits. Instructions are provided on how to make, for example, a nourishing face mask from ground oats, honey, and egg yolks; a three-ingredient moisturizer consisting of coconut oil mixed with lavender and tea-tree essential oils; an "all-natural" deodorant consisting of baking soda, starch, and coconut oil; and countless others. Such combinations may indeed be plant-based and free of synthetic ingredients, but credible and reproducible data demonstrating the efficacy and benefits of such combinations, and a demonstrated understanding of the chemical and biological mechanisms at play, are nowhere to be found.

Another major deterrent associated with the use of botanical ingredients in skincare compositions relates to their relative instability in products. This is evidenced by loss of potency, odor deviations, and discoloration that plague existing "all-natural" formulations. These negative attributes increase the risk of microbial contamination and proliferation, chemical instability, and safety of the products.

In view of the foregoing, there is not an all-natural cosmetic product such as a moisturizer that effectively improves skin health by, for example, properly retaining moisture while omitting synthetic or harmful additives, and that is demonstrated by reproducible and consistent benefits according to credible scientific standards and certifications. Accordingly, there is a need for an all-natural cosmetic product that provides effective skincare using only all-natural ingredients.

SUMMARY

The problem of existing cosmetic compositions including harmful, synthetic, and/or petroleum-based additives, and the problem of existing "all-natural" cosmetic compositions, including moisturizers, lacking rigorous evidence demonstrating their efficacy, is addressed by embodiments of a skincare composition and method of treatment according to the present disclosure.

Embodiments of the present disclosure are directed to a skincare composition intended for enhancing skin health and appearance and containing: (1) a moisturizing/hydrating-effective amount of a mixture of at least: (a) an oil infusion of *Calendula officinalis* extract; (b) an oil infusion of *Helichrysum italicum* extract; (c) an oil infusion of *Symphytum officinale* extract; (d) an aqueous infusion of *Viola tricolor* extract; and (e) an aqueous infusion of at least one *Mallow* extract, such as and/or selected from *Althea officinalis* and/or *Malva sylvestris*; and (2) an emulsifying-effective amount of a dermatologically acceptable emulsifier, wherein the composition is all-natural and free of a skin sensitizing-effective amount of a volatile essential oil.

According to another embodiment, the present disclosure is also directed to a skincare composition intended for enhancing skin health and appearance containing: (1) a natural preservative system; (2) a moisturizing/hydrating-effective amount of a mixture of at least: (a) an oil infusion of *Calendula officinalis* extract; (b) an oil infusion of *Helichrysum italicum* extract; (c) an oil infusion of *Symphytum officinale* extract; (d) an aqueous infusion of *Viola tricolor* extract; and (e) an aqueous infusion of at least one *Mallow* extract, such as and/or selected from *Althea officinalis* and/or *Malva sylvestris*; and (3) an emulsifying-effective amount of a dermatologically acceptable emulsifier, wherein the composition is natural and free of a skin sensitizing-effective amount of a volatile essential oil.

According to further embodiments, the present disclosure is also directed to a skincare composition intended for enhancing skin health and appearance comprising a moisturizing/hydrating-effective amount of a mixture of (1) a natural preservative system; and (2) at least one of an Elderflower hydrosol, infusions of Milk Thistle oil, Castor oil, Safflower oil, and Grapefruit essential oil, and jojoba beads.

According to further embodiments, the present disclosure is also directed to a skincare composition intended for enhancing skin health and appearance comprising a moisturizing/hydrating-effective amount of a mixture of (1) a natural preservative system; and (2) at least one of cucumber, aloe vera, and infusions of Arnica oil and Bladder Wrack oil.

According to further embodiments, the present disclosure is also directed to a skincare composition intended for enhancing skin health and appearance comprising a moisturizing/hydrating-effective amount of a mixture of (1) a natural preservative system; and (2) at least one of *Calendula*-infused oil and water, Serrated Wrack; Hyaluronic acid; Sweet Almond oil; and Green Mandarin oil.

According to further embodiments, the present disclosure is also directed to a skincare composition intended for enhancing skin health and appearance comprising a moisturizing/hydrating-effective amount of a mixture of (1) a natural preservative system; and (2) at least one of Rosehip oil, Bog Myrtle, Sea Buckthorn, Prickly Pear Seed oil, Serrated Wrack, Rosemary, Kiwi Seed oil, and Baobab oil.

The present disclosure is also directed to a method of enhancing skin health and appearance by applying one of the above-disclosed skincare compositions onto the skin.

According to yet another embodiment, the present disclosure is also directed to a method of treating compromised skin by applying one of the above-disclosed skincare compositions onto the skin.

These and other features, aspects and advantages of the present disclosure will become evident to those skilled in the art from a reading of the present disclosure.

DETAILED DESCRIPTION

For purposes of the present disclosure, the use of the word "natural" is intended to encompass ECOCERT®-approved ingredients or formulations synonymous with the terms "green," "clean," "organic," "sustainable," "eco-friendly," or "environmentally-friendly" as known and used in the art. The term "natural," for example, may be used in the context of holistic or homeopathic formulations and is intended to include those topical consumer products and/or preservative systems that are plant-based, paraben-free, and/or non-toxic.

Further, when used in the context of the antimicrobial properties of a preservative or a preservative system, the term "broad spectrum" is intended to describe those preservatives or preservative systems of the present disclosure that have the ability to inhibit the growth of or kill a wide range of microorganisms that decay or spoil topical consumer products. For example, a "broad spectrum" preservative system inhibits the growth of or kills a wide range of bacteria and fungi, preferably a wide range of Gram-positive and Gram-negative bacteria, yeasts, molds, and/or other fungi.

The compositions of the present invention can comprise, consist essentially of, or consist of, the components of the present invention as well as other ingredients described herein. The term "comprising" as used herein is meant to include various optional, compatible components that can be used in the preservative systems and cosmetic compositions of the present disclosure. The term "consisting essentially of" as used herein means that the composition or component may include additional ingredients, but only if the additional ingredients do not materially alter the basic and novel characteristics of the compositions or methods.

As used herein, the words "preferred", "preferably" and variants thereof refer to embodiments of the disclosure that afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the disclosure.

Numerical ranges as used herein are intended to include every number and subset of numbers contained within that range, whether specifically disclosed or not. Further, these numerical ranges should be construed as providing support for a claim directed to any number or subset of numbers within that range.

All percentages, parts, proportions, and ratios as used herein are by weight of the total composition, unless otherwise specified. All such weights as they pertain to listed ingredients are based on the active level.

All references to singular characteristics or limitations of the present disclosure shall include the corresponding plural characteristic or limitation, and vice-versa, unless otherwise specified or clearly implied to the contrary by the context in which the reference is made.

All publications, articles, papers, patents, patent publications and other references cited herein are hereby incorporated in their entireties for all purposes to the extent consistent with the disclosure herein.

The term "compromised skin" as described herein means skin that suffers from symptoms such as dryness, flakiness, itchiness, and irritation. Compromised skin can be caused by extrinsic and/or intrinsic influences, as noted above. Extrinsic influences include, in addition to the influences discussed previously, sunburn, pollution, use of hard-surface cleaning products having harsh chemicals, and mechanical stress associated with shaving and certain dermatological procedures such as laser, microdermabrasion, micro-needling or chemical peel therapy. Intrinsic influences include, in addition to the influences discussed previously, conditions such as eczema and dermatitis. The use of a topical product can effectively moisturize/hydrate the skin in response to such intrinsic influences, thereby alleviating some of the pain and discomfort experienced by individuals suffering from the above-referenced symptoms.

The term "skin-sensitizing effective amount" as described herein is meant to describe an amount of a volatile essential oil that can lead to an allergic response following contact with an individual's skin. Skin sensitization is an immunological response to previous exposure to a substance that results in an inflammatory skin reaction. An allergic skin reaction is usually presented as a red, itchy, bumpy rash. Examples of the types of volatile essential oils that can cause skin sensitization, depending on their amounts within a skincare composition include, but are not limited to, frankincense, myrrh, and sweet orange.

The present disclosure generally relates to a skincare composition that not only effectively enhances skin health and appearance when topically applied thereon, but also serves to help alleviate symptoms associated with compromised skin. Moreover, the skincare composition is also natural, organic and ECOCERT®-approved, thus being free of harmful synthetic and/or petroleum-derived ingredients.

It has surprisingly been discovered by the inventors that a skincare composition that is both all-natural and free of skin-sensitizing ingredients, containing a mixture of specific botanical infusions comprised of at least: an oil infusion of *Calendula officinalis* extract; an oil infusion of *Helichrysum italicum* extract; an oil infusion of *Symphytum officinale* extract; an aqueous infusion of *Viola tricolor* extract; and an aqueous infusion of at least one *Mallow* extract, such as or selected from *Althea officinalis* and/or *Malva sylvestris*, when applied onto skin, both moisturizes and hydrates the skin, and helps the skin retain/lock-in this moisture, thereby enhancing both its health and appearance and, if the skin is also compromised, helps to alleviate symptoms associated therewith.

*Calendula officinalis* extract is derived from the common marigold plant. Common bioactive compounds found therein include, for example, flavonoids, phenolic acids, carotenoids, triterpenic alcohols, polycarbohydrates, proteins, amino acids, saturated hydrocarbons, vitamin C, and mineral substances.

The *Calendula officinalis* extract of the present disclosure is preferably employed in an amount of from about 0.3 to about 0.6% by weight, and most preferably in an amount of about 0.5% by weight, all weights based on the total weight of the skincare composition. The *Calendula officinalis* extract is employed in the form of an oil infusion. The oil component of the infusion is preferably employed in an amount of from about 1 to about 3% by weight, and most preferably in an amount of about 2% by weight, based on the total weight of the composition.

*Calendula officinalis* beneficially brings moisturizing and soothing properties to dry or irritated skin, thereby helping to protect the skin. *Calendula officinalis* stimulates physiological healing and regeneration of wounded skin and aids the skin in retaining hydration. In particular, *Calendula officinalis* improves skin distensibility, firmness, and viscoelasticity, in part by increasing blood flow to the area of application and encouraging tissue regeneration.

*Helichrysum italicum* extract contains numerous bioactive compounds including, for example, phenolics such as heterodimeric phloroglucinyl pyrone arzanol, angeloylated glycerides known as santinols, coumarates, benzofurans, pyrones, and heterodimeric phloroglucinols.

The *Helichrysum italicum* extract of the present disclosure is preferably employed in an amount of from about 0.9 to about 1.3% by weight, and most preferably in an amount of about 1.2% by weight, all weights based on the total weight of the skincare composition. The *Helichrysum italicum* extract is employed in the form of an oil infusion. The oil component of the infusion is preferably employed in an amount of from about 4 to about 7% by weight, and most preferably in an amount of about 4.7% by weight, based on the total weight of the composition.

*Helichrysum italicum* has emollient properties and creates a protective film to retain moisture and keep the skin hydrated.

The primary bioactive compounds found in *Symphytum officinale* extract include allantoin, rosmarinic acid and ellagic acid.

The *Symphytum officinale* extract of the present disclosure is preferably employed in an amount of from about 0.3 to about 0.6% by weight, and most preferably in an amount of about 0.5% by weight, all weights based on the total weight of the skincare composition. The *Symphytum officinale* extract is employed in the form of an oil infusion. The oil component of the infusion is preferably employed in an amount of from about 1 to about 3% by weight, and most preferably in an amount of about 2% by weight, based on the total weight of the composition.

*Symphytum officinale* provides keratolytic properties to shed dry, outer layers of the epidermis, thereby helping to maintain a healthy level of moisture and an improved appearance of the skin.

While any vegetable oil may be used as the oil component in the above-described oil infusions so long as it does not cause skin sensitization, a particularly preferred oil component is almond oil. The inventors have surprisingly discovered that the use of almond oil enables bioactive compounds present in the oil infusions to effectively penetrate into the skin, without the need to use skin-sensitizing essential oils, and while still facilitating the desired degree of efficacy in terms of skin health and appearance resulting from enhanced moisturization and hydration of the skin. This is due to almond oil being rich in beta-zoosterol, squalene, and alpha-tocopherol, together with smaller amounts of carbohydrates, proteins, vitamins, and minerals such as vitamin B complex and zinc. Almond oil's phytochemicals are believed to be effective at promoting surface-level proliferation and skin cell development. Other vegetable oils that may be used include, but are not limited to, olive oil, jojoba oil, babassu oil, caster oil, coconut oil, corn oil, cotton seed oil, linseed oil, mustard oil, safflower oil, sesame oil, soybean oil, sunflower-seed oil, wheat germ oil, argan oil and marula oil.

Some interesting bioactive compounds found in *Viola tricolor* extract include small peptides known as cyclotides, flavonoids such as quercetin, luteolin and rutin, mucilages consisting of glucose, galactose, arabinose and rhamnose, as well as tannins and salicylic acid and its derivatives.

The *Viola tricolor* extract of the present disclosure is preferably employed in an amount of from about 2 to about 3% by weight, and most preferably in an amount of about 2.5% by weight, all weights based on the total weight of the composition. The *Viola tricolor* extract is employed in the form of an aqueous infusion.

*Viola tricolor* advantageously provides polysaccharides to boost the skin's capacity to retain water by improving osmotic function.

The at least one *Mallow* extract of the present disclosure will preferably be chosen from *Malva sylvestris* extract and *Althea officinalis* extract. These *Mallow* extracts possess an abundance of mucilages having polysaccharides contained therein. These mucilages consist mainly of glucuronic acid, galacturonic acid, rhamnose, galactose, fructose, glucose, sucrose and trehalose, as well as lesser amounts of uronic acid, arabinose, mannose, xylose, fucose, raffinose and 2-O-α-(4-O-methyl-α-d-glucuronosyl)-xylotriose.

The at least one *Mallow* extract of the present disclosure is preferably employed in an amount of from about 2 to about 3% by weight, and most preferably in an amount of about 2.5% by weight, all weights based on the total weight of the skincare composition. A particularly preferred *Mallow* extract is *Althea officinalis* extract. The *Mallow* extract is employed in the form of an aqueous infusion.

The at least one *Mallow* extract forms a soothing protective gel that moisturizes dry, rough skin due to its mucilaginous properties, which form a thick, gluey substance.

Both the *Viola tricolor* and *Mallow* extracts are employed as aqueous infusions, wherein the total water content of both aqueous infusions is from about 50 to about 70% by weight, and preferably about 60% by weight, all weights based on the total weight of the skincare composition.

By providing a skincare composition comprising a combination of *Calendula officinalis*, *Helichrysum italicum*, and *Symphytum officinale* oil infusions and *Viola tricolor* and *Mallow* aqueous extracts, the skincare composition hydrates, soothes, and nourishes a user's skin in complementary ways. The skincare composition soothes the skin with *Calendula officinalis*, creates a protective moisture-retaining film with *Helichrysum italicum*, helps the skin shed dry outer layers of epidermis with *Symphytum officinale*, improves osmotic function with *Viola tricolor*, and forms a moisturizing and soothing protective gel with *Mallow* extract. The skincare composition's combination of botanical oil infusions with botanical aqueous extracts, held together by a natural and dermatologically favorable emulsifier, avoids the problem created by synthetic and petroleum-based moisturizers, which are oppressively occlusive and interfere with normal skin function. The skincare composition benefits normal skin function by providing healing and/or nourishing compounds to protect the skin across a range of physiological functions, including shedding of dry epidermis layers, improving moisture retention, and forming natural protective films and gels to augment and supplement the skin's biological moisturizing properties.

*Calendula officinalis*, *Helichrysum italicum*, *Symphytum officinale*, *Viola tricolor*, and *Mallow* are further provided in specific, effective, synergistic, and targeted amounts for user health, comfort, cost, and compatibility. Moreover, as discussed in greater detail herein, the benefits and efficacy of the composition are quantifiable, reproducible, and rigorously obtained.

The botanical oil infusions of the present disclosure are obtained using an extraction technique known as maceration. This technique, typically performed at room temperature, involves immersing a plant in oil which functions as a solvent inside an airtight vessel for a variable amount of time based on the plant material being infused into the oil.

The vessel in which the plant material is being macerated is periodically agitated in order to aid the solvent in penetrating the outer cell walls of the plant material. Once the plant material has been sufficiently infused with the solvent, the resultant macerated product is then filtered in order to separate the residual plant material from the liquid. The residual plant material is then pressed in order to recover any excess liquid entrapped therein.

The botanical aqueous infusions of the present disclosure are obtained using an extraction technique known as decoction. This technique involves immersing a plant in boiling water, preferably purified water, inside an airtight vessel, for a variable amount of time based on the plant material being infused into the water.

Prior to being processed, the plant is first properly washed and separated from any foreign material such as topsoil, pebbles or rocks, weeds, and other materials not suitable for extraction. The plant material should be used fresh in order to maintain the integrity of the bioactive components in the fresh plant matter. The use of dried plant material is typically not desirable due to the degradation experienced by the plant during the dehydration process. During dehydration, the cell walls are compromised resulting in the degradation of compounds through mechanisms such as hydrolysis, oxidation, polymerization, Maillard reactions, and isomerization. When the dried plant undergoes extraction, the resulting extract contains these degradation products that were not in the fresh plant matter. The presence of these degradation products can negatively impact the efficacy of the product and increase the potential for skin sensitization.

In order to maximize the contact between the plant material to be macerated and the oil, the plant is preferably cut into small pieces. The pieces should not be too big, otherwise the oil will not be able to penetrate the plant's innermost cells. The pieces should also not be reduced to powder, as that would make it more difficult to separate the infusion from the bulk plant material via filtration once the maceration process is completed.

Because the skincare composition of the present disclosure comprises a mixture of both oil infusions and aqueous infusions, an emulsifier should also be employed in order to emulsify the immiscible oil and aqueous phases of the skincare composition. Any ingredient capable of emulsifying the composition may be employed without departing from the spirit of the disclosure so long as it is natural and dermatologically acceptable. Suitable emulsifiers include, but are not limited to, glyceryl stearate, cetyl alcohol, sodium stearoyl lactylate, sorbitan olivate, cetearyl olivate, cetearyl alcohol, cetearyl glucoside, sodium cetearyl sulfate, and the like. It is also particularly preferred that the emulsifier be free of palm oil.

According to one embodiment of the present disclosure, there is provided a skincare composition for application onto human skin in order to enhance its health and appearance, the composition containing a moisturizing/hydrating-effective amount of a mixture of at least: (a) an oil infusion of *Calendula officinalis* having from about 0.3 to about 0.6% by weight, and preferably about 0.5% by weight, of *Calendula officinalis* extract, and from about 1 to about 3% by weight, and preferably about 2% by weight of a vegetable oil, preferably almond oil; (b) an oil infusion of *Helichrysum italicum* having from about 0.9 to about 1.3% by weight, and preferably about 1.2% by weight, of *Helichrysum italicum* extract, and from about 4 to about 7% by weight, and preferably about 4.7% by weight of a vegetable oil, preferably almond oil; (c) an oil infusion of *Symphytum officinale* having from about 0.3 to about 0.6% by weight, and preferably about 0.5% by weight, of *Symphytum officinale* extract, and from about 1 to about 3% by weight, and preferably about 2% by weight, of a vegetable oil, preferably almond oil; (d) an aqueous infusion of *Viola tricolor* having from about 2 to about 3% by weight, and preferably about 2.5% by weight, of *Viola tricolor* extract; and (e) an aqueous infusion of at least one *Mallow* extract chosen from *Althea officinalis* and *Malva sylvestris*, having from about 2 to about 3% by weight, and preferably about 2.5% by weight, of *Mallow* extract, wherein aqueous infusions (d) and (e) have a total water content of from about 50 to about 70% by weight, and preferably about 60% by weight, all weights being based on the total weight of the composition; and an emulsifying-effective amount of a dermatologically acceptable emulsifier, wherein the composition is natural and free of a skin sensitizing-effective amount of a volatile essential oil.

In another embodiment of the present disclosure, the inventors have surprisingly discovered that a natural preservative system comprised of a combination of specific amounts of: a *Lactobacillus* ferment, a *Lactobacillus* and *Cocos nucifera* (coconut) fruit extract, salicylic acid (in some embodiments optional), a salt of a weak acid such as potassium sorbate, and a petroleum-free propanediol, when incorporated into a composition having a specific pH range, effectively both prohibits and inhibits microbial growth on and in the composition.

The *Lactobacillus* ferment of the present disclosure is preferably employed in an amount of from about 1 to about 5% by weight, preferably from about 2 to about 4% and more preferably from about 2 to about 4%, by weight of the total composition. An exemplary *Lactobacillus* ferment is commercially available from Active Micro Technologies under the tradename Leucidal® SF.

The *Lactobacillus* and *Cocos nucifera* fruit extract can include any *Cocos nucifera* fruit extract fermented with *Lactobacillus* and/or included with *Lactobacillus* ferment of the present disclosure and is preferably employed in an amount of from about 1 to about 5%, preferably from about 2 to about 4%, by weight of the total composition. An exemplary *Lactobacillus* and *Cocos nucifera* extract is commercially available from Active Micro Technologies under the tradename Amticide® Coconut and is typically associated with the International Nomenclature of Cosmetic Ingredients (INCI) name of a *Lactobacillus* and *Cocos nucifera* (coconut) fruit extract.

When present, salicylic acid is preferably employed in an amount of up to about 0.5% by weight, preferably from about 0.1 to about 0.45% and more preferably from about 0.2 to about 0.4%, by weight of the total composition. It should be noted that the use of salicylic acid in an amount at or greater than about 0.5% by weight, based on the total weight of the composition, renders the composition a drug requiring FDA approval in the prior to commercialization and sale in the United States. In some embodiments, salicylic acid may be omitted by adjusting the concentrations of *Lactobacillus* ferment, *Lactobacillus* and *Cocos nucifera* fruit extract, and/or other ingredients as described in greater detail herein.

The salt of a weak acid is preferably employed in an amount of up to about 0.5% by weight, preferably from about 0.1 to about 0.45% and more preferably from about 0.2% to about 0.4%, by weight of the total composition. A preferred salt of a weak acid is potassium sorbate (i.e., the potassium salt of sorbic acid). Other weak acids that may be used in their salt form include, but are not limited to, acetic acid, propionic acid, and benzoic acid.

Petroleum-free 1,3-propanediol is typically employed in an amount of about 1% to about 10% by weight, preferably from about 2% to about 8% and more preferably from about 4% to about 6%, by weight of the total composition. An exemplary petroleum-free 1,3-propanediol is commercially available from Dupont Tate & Lyle Bio Products under the tradename Zemea® Propanediol and can be associated with the INCI name propanediol.

The inventors have unexpectedly discovered that the ability of the preservative system of the present disclosure to effectively inhibit microorganism growth is critically dependent on the pH of the composition in which it is used. For example, if the preservative system is employed in a composition having a pH of 6, it fails to provide the requisite broad-spectrum protection needed for acceptable storage stability/shelf-life. Accordingly, the pH of a composition containing the preservative system of the present disclosure must be in a range of from about 4.5 to about 5.5, and preferably from about 4.8 to about 5.3.

According to this embodiment of the present disclosure, there is provided a skincare composition intended for application onto human skin in order to enhance its health and appearance, the composition containing: (1) a preservative system that includes: (a) from about 1 to about 5%, preferably from about 2 to about 4%, by weight of a *Lactobacillus* ferment; (b) from about 1 to about 5%, preferably from about 2 to about 4%, by weight of a *Lactobacillus* and *Cocos nucifera* fruit extract; (c) up to about 0.5%, preferably from about 0.1 to about 0.45% and more preferably from about 0.2 to about 0.4%, by weight of salicylic acid; (d) from about 0.1 to about 0.5% by weight, and preferably from about 0.2 to about 0.4% by weight of at least one salt of a weak acid, preferably potassium sorbate; and (e) from about 1 to about 10%, preferably from about 2 to about 8% and more preferably from about 4 to about 6%, by weight of a petroleum-free propanediol, preferably 1,3-propanediol; (2) a moisturizing/hydrating-effective amount of a mixture of at least: (f) an oil infusion of *Calendula officinalis* having from about 0.3 to about 0.6% by weight, and preferably about 0.5% by weight, of *Calendula officinalis* extract, and from about 1 to about 3% by weight, and preferably about 2% by weight of a vegetable oil, preferably almond oil; (g) an oil infusion of *Helichrysum italicum* having from about 0.9 to about 1.3% by weight, and preferably about 1.2% by weight, of *Helichrysum italicum* extract, and from about 4 to about 7% by weight, and preferably about 4.7% by weight of a vegetable oil, preferably almond oil; (h) an oil infusion of *Symphytum officinale* having from about 0.3 to about 0.6% by weight, and preferably about 0.5% by weight, of *Symphytum officinale* extract, and from about 1 to about 3% by weight, and preferably about 2% by weight of a vegetable oil, preferably almond oil; (i) an aqueous infusion of *Viola tricolor* having from about 2 to about 3% by weight, and preferably about 2.5% by weight, of *Viola tricolor* extract; and (j) an aqueous infusion of at least one *Mallow* extract chosen from *Althea officinalis* and *Malva sylvestris* having from about 2 to about 3% by weight, and preferably about 2.5% by weight, of *Mallow* extract, wherein aqueous infusions (i) and (j) have a total water content of from about 50 to about 70% by weight, and preferably about 60% by weight, all weights being based on the total weight of the composition; and (3) an emulsifying-effective amount of a dermatologically acceptable emulsifier, wherein the composition is natural, free of a skin sensitizing-effective amount of a volatile essential oil, and has a pH ranging from about 4.5 to about 5.5, preferably from about 4.8 to about 5.3.

In another embodiment of the present disclosure, there is provided a skincare composition intended for application onto human skin in order to enhance its health and appearance, the composition containing: (1) a preservative system that includes: (a) from about 1 to about 5%, preferably from about 2 to about 4%, by weight of a *Lactobacillus* ferment; (b) from about 1 to about 5%, preferably from about 2 to about 4%, by weight of a *Lactobacillus* and *Cocos nucifera* fruit extract; (c) from about 0.1 to about 0.45% by weight, preferably from about 0.2 to about 0.4% of salicylic acid; (d) up to about 0.5% by weight, preferably from about 0.2 to about 0.4% by weight, of at least one salt of a weak acid, preferably potassium sorbate; and (e) from about 1 to about 10%, preferably from about 2 to about 8% by weight, and most preferably from about 4 to about 6% by weight, of a petroleum-free propanediol; (2) a moisturizing/hydrating-effective amount of a mixture of at least: (f) an oil infusion of *Calendula officinalis* having from about 0.3 to about 0.6% by weight, and preferably about 0.5% by weight, of *Calendula officinalis* extract, and from about 1 to about 3% by weight, and preferably about 2% by weight of a vegetable oil, preferably almond oil; (g) an oil infusion of *Helichrysum italicum* having from about 0.9 to about 1.3% by weight, and preferably about 1.2% by weight, of *Helichrysum italicum* extract, and from about 4 to about 7% by weight, and preferably about 4.7% by weight of a vegetable oil, preferably almond oil; (h) an oil infusion of *Symphytum officinale* having from about 0.3 to about 0.6% by weight, and preferably about 0.5% by weight, of *Symphytum officinale* extract, and from about 1 to about 3% by weight, and preferably about 2% by weight of a vegetable oil, preferably almond oil; (i) an aqueous infusion of *Viola tricolor* having from about 2 to about 3% by weight, and preferably about 2.5% by weight, of *Viola tricolor* extract; and (j) an aqueous infusion of at least one *Mallow* extract chosen from *Althea officinalis* and *Malva sylvestris* having from about 2 to about 3% by weight, and preferably about 2.5% by weight, of *Mallow* extract, wherein aqueous infusions (i) and (j) have a total water content of from about 50 to about 70% by weight, and preferably about 60% by weight, all weights being based on the total weight of the composition; and (3) an emulsifying-effective amount of a dermatologically acceptable emulsifier, wherein the composition is natural, free of a skin sensitizing-effective amount of a volatile essential oil, and has a pH ranging from about 4.5 to about 5.5, and preferably from about 4.8 to about 5.3.

According to yet another embodiment of the present disclosure, there is provided a skincare composition intended for application onto human skin in order to enhance its health and appearance, the composition containing: (1) a preservative system that includes: (a) from about 1 to about 5%, preferably from about 2 to about 4% by weight, of a *Lactobacillus* ferment; (b) from about 1 to about 5%, preferably from about 2 to about 4% by weight, of a *Lactobacillus* and *Cocos nucifera* fruit extract; (c) from about 0.1 to about 0.45%, preferably from about 0.2 to about 0.4% by weight, of salicylic acid; (d) from about 0.1 to about 0.5% by weight, preferably from about 0.2 to about 0.4% by weight, of at least one salt of a weak acid, preferably potassium sorbate; and (e) from about 1 to about 10%, preferably from about 2 to about 8%, and most preferably from about 4 to about 6% by weight, of a petroleum-free propanediol; (2) a moisturizing/hydrating-effective amount of a mixture of at least: (f) an oil infusion of *Calendula officinalis* having from about 0.3 to about 0.6% by weight, and preferably about 0.5% by weight, of *Calendula officinalis* extract, and from about 1 to about 3% by weight, and preferably about 2% by weight of a vegetable oil, preferably almond oil; (g) an oil infusion of *Helichrysum italicum* having from about 0.9 to about 1.3% by weight, and preferably about 1.2% by weight, of *Helichrysum italicum* extract, and from about 4 to about 7% by weight, and preferably about 4.7% by weight of a vegetable oil, preferably almond oil; (h) an oil infusion of *Symphytum officinale* having from about 0.3 to about 0.6% by weight, and preferably about 0.5% by weight, of *Symphytum officinale* extract, and from about 1 to about 3% by weight, and preferably about 2% by weight of a vegetable oil, preferably almond oil; (i) an aqueous infusion of *Viola tricolor* having from about 2 to about 3% by weight, and preferably about 2.5% by weight, of *Viola tricolor* extract; and (j) an aqueous infusion of at least one *Mallow* extract chosen from *Althea officinalis* and *Malva sylvestris* having from about 2 to about 3% by weight, and preferably about 2.5% by weight, of *Mallow* extract, wherein aqueous infusions (i) and (j) have a total water content of from about 50 to about 70% by weight, and preferably about 60% by weight, all weights being based on the total weight of the composition; and (3) an emulsifying-effective amount of a dermatologically acceptable emulsifier, wherein the composition is natural, free of a skin sensitizing-effective amount of a volatile essential oil, and has a pH ranging from about 4.5 to about 5.5, and preferably from about 4.8 to about 5.3.

In yet another embodiment of the present disclosure, there is provided a skincare composition intended for application onto human skin in order to enhance its health and appearance, the composition containing: (1) a preservative system comprised of: (a) from about 2 to about 4% by weight, of a *Lactobacillus* ferment; (b) from about 2 to about 4% by weight, of a *Lactobacillus* and *Cocos nucifera* fruit extract; (c) from about 0.2 to about 0.4% by weight, of salicylic acid; (d) from about 0.2 to about 0.4% by weight, of at least one salt of a weak acid, preferably potassium sorbate; and (e) from about 4 to about 6% by weight, of a petroleum-free propanediol; (2) a moisturizing/hydrating-effective amount of a mixture of at least: (f) an oil infusion of *Calendula officinalis* having from about 0.3 to about 0.6% by weight, and preferably about 0.5% by weight, of *Calendula officinalis* extract, and from about 1 to about 3% by weight, and preferably about 2% by weight of a vegetable oil, preferably almond oil; (g) an oil infusion of *Helichrysum italicum* having from about 0.9 to about 1.3% by weight, and preferably about 1.2% by weight, of *Helichrysum italicum* extract, and from about 4 to about 7% by weight, and preferably about 4.7% by weight of a vegetable oil, preferably almond oil; (h) an oil infusion of *Symphytum officinale* having from about 0.3 to about 0.6% by weight, and preferably about 0.5% by weight, of *Symphytum officinale* extract, and from about 1 to about 3% by weight, and preferably about 2% by weight of a vegetable oil, preferably almond oil; (i) an aqueous infusion of *Viola tricolor* having from about 2 to about 3% by weight, and preferably about 2.5% by weight, of *Viola tricolor* extract; and (j) an aqueous infusion of at least one *Mallow* extract chosen from *Althea officinalis* and *Malva sylvestris* having from about 2 to about 3% by weight, and preferably about 2.5% by weight, of *Mallow* extract, wherein aqueous infusions (i) and (j) have a total water content of from about 50 to about 70% by weight, and preferably about 60% by weight, all weights being based on the total weight of the composition; and (3) an emulsifying-effective amount of a dermatologically acceptable emulsifier, wherein the composition is natural, free of a skin sensitizing-effective amount of a volatile essential oil, and has a pH ranging from about 4.5 to about 5.5, and preferably from about 4.8 to about 5.3.

According to another embodiment of the present disclosure, there is provided a skincare composition intended for application onto human skin in order to enhance its health and appearance, the composition containing: (1) a preservative system comprised of: (a) from about 2 to about 4% by weight, of a *Lactobacillus* ferment; (b) from about 2 to about 4% by weight, of a *Lactobacillus* and *Cocos nucifera* fruit extract; (c) from about 0.2 to about 0.4% by weight, of salicylic acid; (d) from about 0.2 to about 0.4% by weight, of at least one salt of a weak acid, preferably potassium sorbate; and (e) from about 4 to about 6% by weight, of a petroleum-free propanediol; (2) a moisturizing/hydrating-effective amount of a mixture of at least: (f) an oil infusion of *Calendula officinalis* having about 0.5% by weight of *Calendula officinalis* extract, and about 2% by weight of almond oil; (g) an oil infusion of *Helichrysum italicum* having about 1.2% by weight, of *Helichrysum italicum* extract, and about 4.7% by weight of almond oil; (h) an oil infusion of *Symphytum officinale* having about 0.5% by weight, of *Symphytum officinale* extract, and about 2% by weight of almond oil; (i) an aqueous infusion of *Viola tricolor* having about 2.5% by weight, of *Viola tricolor* extract; and (j) an aqueous infusion of at least one *Mallow* extract chosen from *Althea officinalis* and *Malva sylvestris* having about 2.5% by weight, of *Mallow* extract, wherein aqueous infusions (i) and (j) have a total water content of about 60% by weight; and (3) about 8.5% by weight of a dermatologically acceptable emulsifier, all weights being based on the total weight of the composition, wherein the composition is natural, free of a skin sensitizing-effective amount of a volatile essential oil, and has a pH ranging from about 4.5 to about 5.5, and preferably from about 4.8 to about 5.3.

According to another embodiment of the present disclosure, there is provided a skincare composition intended for application onto human skin in order to enhance its health and appearance, the composition containing: (1) a preservative system comprised of: (a) about 4% by weight, of a *Lactobacillus* ferment; (b) about 4% by weight, of a *Lactobacillus* and *Cocos nucifera* fruit extract; (c) about 0.4% by weight, of potassium sorbate; and (e) about 4% by weight, of a petroleum-free propanediol; (2) a moisturizing/hydrating-effective amount of a mixture of at least: (f) an oil infusion of *Calendula officinalis* having about 0.5% by weight of *Calendula officinalis* extract, and about 2% by weight of almond oil; (g) an oil infusion of *Helichrysum italicum* having about 1.2% by weight, of *Helichrysum italicum* extract, and about 4.7% by weight of almond oil; (h) an oil infusion of *Symphytum officinale* having about 0.5% by weight, of *Symphytum officinale* extract, and about 2% by weight of almond oil; (i) an aqueous infusion of *Viola tricolor* having about 2.5% by weight, of *Viola tricolor* extract; and (j) an aqueous infusion of at least one *Mallow* extract chosen from *Althea officinalis* and *Malva sylvestris* having about 2.5% by weight, of *Mallow* extract, wherein aqueous infusions (i) and (j) have a total water content of about 60% by weight; and (3) about 8.5% by weight of a dermatologically acceptable emulsifier, all weights being based on the total weight of the composition, wherein the composition is natural, free of a skin sensitizing-effective amount of a volatile essential oil, and has a pH ranging from about 4.5 to about 5.5, preferably from about 4.8 to about 5.3.

According to further embodiments of the disclosure, a skincare composition may comprise (1) a preservative system comprised of: (a) about 4% by weight, of a *Lactobacillus* ferment; (b) about 4% by weight, of a *Lactobacillus* and *Cocos nucifera* fruit extract; (c) about 0.4% by weight, of potassium sorbate; and (e) about 4% by weight, of a petroleum-free propanediol; (2) an Elderflower hydrosol, infusions of Milk Thistle oil, Castor oil, Safflower oil, and Grapefruit essential oil, and jojoba beads; (3) about 8.5% by weight of a dermatologically acceptable emulsifier; and (4) a dermatologically acceptable carrier, all weights being based on the total weight of the composition, wherein the composition is natural, free of a skin sensitizing-effective amount of an essential oil, free of petroleum-derived ingredients, and has a pH ranging from about 4.5 to about 5.5, preferably from about 4.8 to about 5.3.

Elderflower hydrosol provides plant acids that gently tone the skin. Milk Thistle oil comprises antioxidant properties to protect the skin, e.g. from UV radiation. Castor and Safflower oil reduce pore size, increase hydration, and offer superior cleansing abilities. Grapefruit essential oil provides an uplifting scent with toning properties. Jojoba beads provide light exfoliation without causing skin irritation.

In another embodiment of the disclosure, a composition intended for application onto human skin in order to enhance its health and appearance is provided, the composition comprising: (1) a preservative system comprised of: (a) about 4% by weight, of a *Lactobacillus* ferment; (b) about 4% by weight, of a *Lactobacillus* and *Cocos nucifera* fruit extract; (c) about 0.4% by weight, of potassium sorbate; and (e) about 4% by weight, of a petroleum-free propanediol; (2) *Helichrysum italicum*, cucumber, aloe vera, and infusions of Arnica oil and Bladder Wrack oil; (3) about 8.5% by weight of a dermatologically acceptable emulsifier; and (4) a dermatologically acceptable carrier, all weights being based on the total weight of the composition, wherein the composition is natural, free of a skin sensitizing-effective amount of an essential oil, free of petroleum-derived ingredients, and has a pH ranging from about 4.5 to about 5.5, preferably from about 4.8 to about 5.3.

Arnica oil reduces puffiness around the eyes. Bladder Wrack oil helps reduce moisture loss and protects the skin against irritation. *Helichrysum italicum* advantageously provides a moisture-retentive film to keep the skin hydrated, while cucumber provides amino acids, proteins, and lipids that help to pump and calm the skin. Aloe vera soothes and hydrates the skin while increasing firmness.

In another embodiment of the disclosure, a composition intended for application onto human skin in order to enhance its health and appearance is provided, the composition comprising: (1) a preservative system comprised of: (a) about 4% by weight, of a *Lactobacillus* ferment; (b) about 4% by weight, of a *Lactobacillus* and *Cocos nucifera* fruit extract; (c) about 0.4% by weight, of potassium sorbate; and (e) about 4% by weight, of a petroleum-free propanediol; (2) *Calendula*-infused oil and water, Serrated Wrack, Hyaluronic acid from about 1 to about 3% by weight, Sweet Almond oil, and Green Mandarin oil; (3) about 8.5% by weight of a dermatologically acceptable emulsifier; and (4) a dermatologically acceptable carrier, all weights being based on the total weight of the composition, wherein the composition is natural, free of a skin sensitizing-effective amount of an essential oil, free of petroleum-derived ingredients, and has a pH ranging from about 4.5 to about 5.5, preferably from about 4.8 to about 5.3.

*Calendula*-infused oil and water improve skin distensibility, firmness, and viscoelasticity. Serrated Wrack improves skin suppleness by moisturizing and improving the skin barrier. Hyaluronic acid, in a range from, for example, about 1% by weight to about 3% by weight, boosts the skin's ability to absorb moisture and results in smoother, softer skin. Sweet Almond oil softens the skin. Green Mandarin oil tones and helps balance oil production in the skin.

In another embodiment of the disclosure, a composition intended for application onto human skin in order to enhance its health and appearance is provided, the composition comprising: (1) a preservative system comprised of: (a) about 4% by weight, of a *Lactobacillus* ferment; (b) about 4% by weight, of a *Lactobacillus* and *Cocos nucifera* fruit extract; (c) about 0.4% by weight, of potassium sorbate; and (e) about 4% by weight, of a petroleum-free propanediol; (2) Rosehip oil, Bog Myrtle, Sea Buckthorn, Prickly Pear Seed oil, Serrated Wrack, Rosemary, Kiwi Seed oil, and Baobab oil; (3) about 8.5% by weight of a dermatologically acceptable emulsifier; and (4) a dermatologically acceptable carrier, all weights being based on the total weight of the composition, wherein the composition is natural, free of a skin sensitizing-effective amount of an essential oil, free of petroleum-derived ingredients, and has a pH ranging from about 4.5 to about 5.5, preferably from about 4.8 to about 5.3.

Rosehip oil soothes, moisturizes, and softens the skin, and further contains Vitamins A and C. It is also rich in essential fatty acids. Bog Myrtle helps keep pores clean and provides antioxidants. Sea Buckthorn helps retain moisture and improve skin elasticity, and further contains vitamins, minerals, and omega-3 fatty acids. Prickly Pear Seed oil reduces hyperpigmentation, and further contains vitamins E and K and is rich in essential fatty acids. Serrated Wrack helps improve the suppleness and elasticity of the skin, and contains minerals and trace elements. Rosemary protects the skin from environmental stressors. Kiwi Seed oil controls sebum production and helps maintain clear skin. Baobab oil gives elasticity to the skin and contains vitamins A, D, E, and F.

The skincare compositions of the present disclosure may be in a wide variety of product forms that include, but are not limited to, solutions, suspensions, lotions, creams, gels, sprays, ointments and serums. For example, a product intended for application onto skin, post-shaving, in order to help relieve the irritation associated with the mechanical stress on the skin caused by the shaving process, can be formulated using the above-described compositions as a base formula.

According to embodiments of the present disclosure, the skincare compositions can comprise other suitable, optional ingredients as desired. For example, the composition can optionally include other active or inactive ingredients, provided they do not unacceptably alter the benefits of the skincare composition, are natural, and do not promote skin sensitization. The precise amount of optional ingredients will be determined by those skilled in the art. Examples of other ingredients that may be employed include, but are not limited to, humectants, emollients, flavonoids, minerals, chelating agents, pH regulators/buffers, rheology modifiers, phytosterols, vitamin B3 compound, anti-inflammatory agents such as licorice extracts, bisabolol, manjistha extracted from plants in the genus *Rubia*, guggal extracted from plants in the genus *Commiphora, Quillaja saponaria* extract, kola extract, chamomile, red clover extract, sea whip extract, hibiscus extract, lucuma extract, sea kale extract, Iceland Moss extract, Saskatoon Berry extract, Siberian Ginseng extract, spruce needles extract, birch bark extract, blueberry extract, cranberry extract, yarrow extract, marigold extract and couch grass extract.

Additional ingredients that may be employed in order to further potentiate the efficacy of embodiments of the disclosure may include, for example, *Astrocaryum murumuru* seed butter, *Theobroma grandiflorum* seed butter, *Spondias mombin* pulp extract, *Mangifera indica* pulp extract, *Musa sapientum* pulp extract, *Mauritia flexuosa* fruit oil, *Physalis angulata* extract, *Xylityl sesquicaprylate, Vaccinium myrtil-* lus seed oil, *Cucubita pepo* seed extract, linoleic acid, *Centella asiatica* leaf extract, *Tamarindus indica* seed polysaccharide, *Zanthoxylum bungeanum* fruit extract, *Lactococcus* ferment lysate, *Bellis perennis* flower extract, *Coffea arabica* seed cake extract, *Coffea arabica* seed oil, cotton seed oil, linseed oil, *Pichia* ferment lysate filtrate, and whey protein.

The dermatologically acceptable carrier can encompass a wide variety of forms. In some cases, the solubility or dispersibility of the components in the composition may dictate the form and character of the carrier. Non-limiting examples include simple solutions (e.g., aqueous or anhydrous), dispersions, emulsions and solid forms. In certain embodiments, the dermatologically acceptable carrier is in the form of an emulsion. An emulsion can be generally classified as having a continuous aqueous phase (e.g., oil-in-water and water-in-oil-in-water) or a continuous oil phase (e.g., water-in-oil or oil-in-water). While the oil phase may comprise any vegetable oil, so long as it does not cause skin sensitization, a particularly preferred oil component is almond oil. The inventors have surprisingly discovered that the use of almond oil enables bioactive compounds present in the botanical extract to effectively penetrate into the skin, without the need of having to use skin-sensitizing essential oils, while still facilitating the desired degree of efficacy. This is due to almond oil being rich in beta-zoosterol, squalene, and alpha-tocopherol, together will lesser amounts of carbohydrates, proteins, vitamins and minerals such as vitamin B complex and zinc. Moreover, almond oil's phytochemicals are believed to be effective at promoting surface level proliferation and skin cell development. Other vegetable oils that may also be used include, but are not limited to, olive oil, jojoba oil, babassu oil, caster oil, coconut oil, corn oil, cotton seed oil, linseed oil, mustard oil, safflower oil, sesame oil, soybean oil, sunflower-seed oil, wheat germ oil, argan oil and marula oil.

As has been noted above, individuals at times suffer from compromised skin that can be caused by extrinsic and/or intrinsic influences. In those instances, the use of a topical product capable of moisturizing, hydrating and soothing the skin in order to alleviate symptoms associated with this condition is highly desirable. Although there are a number of products commercially available for addressing this condition, they oftentimes contain synthetic ingredients. One example of just such a product is EUCERIN® commercially available from Beiersdorf of Hamburg, Germany. For those individuals wanting to avoid applying any synthetic, potentially skin-sensitizing ingredients onto already compromised skin, topical products that are natural, organic, ECO-CERT®-approved, yet efficacious are needed.

Thus, according to yet another embodiment, the present disclosure is also directed to a method of treating compromised skin by applying one of the above-disclosed compositions onto the compromised skin.

EXAMPLES

The following examples as set forth herein are intended for illustrative purposes only and are not intended to limit the scope of the disclosure in any way, as many variations thereof are possible without departing from the spirit and scope of the disclosure. In the examples, all concentrations are listed as weight percent, unless otherwise specified.

Example 1

| Ingredients | % wt/wt | % extract | % almond oil |
|---|---|---|---|
| *Helichrysum italicum* | 5.9 | 1.2 | 4.7 |
| *Calendula officinalis* | 2.5 | 0.5 | 2.0 |
| *Symphytum officinale* | 2.5 | 0.5 | 2.0 |
| emulsifiers | 8.5 | | |
| *Lactobacillus* ferment | 4.0 | | |
| *Lactobacillus* and *Cocos nucifera* fruit extract | 4.0 | | |
| Potassium sorbate | 0.4 | | |
| 1,3-propanediol | 4.0 | | |
| *Viola tricolor* | 2.5 | | |
| *Althea officinalis* | 2.5 | | |
| Purified water | 60.9 | | |
| Additives | q.s. | | |
| Total | 100 | | |

The composition of Example 1 was clinically tested in order to determine its efficacy in enhancing skin health and appearance. Thirty-six individuals aged 45-65 were asked to apply the composition twice a day at home, once in the morning and once in the evening, under normal use conditions, as a replacement for their normal skin treatment routine. Skin health and appearance data were collected on day zero, day 28, day 56, and day 84.

The skin-smoothing and anti-wrinkle effect of the composition was determined in-vivo using the fringe projection system DermaTOP® and its attendant acquisition software. This system measures the height of projections in µm emanating from the skin used to assess skin roughness and severity of wrinkles on the skin. A decrease in projection height evidences smoother, less wrinkled skin. The data clearly evidence the skin-smoothing/anti-wrinkling effect of the composition, as shown in Table 1 below.

TABLE 1

| Parameters and Kinetics | Δ% on mean | % of subjects with the expected effect |
|---|---|---|
| Average Roughness (µm) D28 | −1% | 56% |
| Average Roughness (µm) D56 | +1% | 45% |
| Average Roughness (µm) D84 | −5% | 72% |
| Average Relief (µm) D28 | −2% | 56% |
| Average Relief (µm) D56 | +1% | 42% |
| Average Relief (µm) D84 | −5% | 69% |
| Maximum relief amplitude (µm) D28 | −2% | 50% |
| Maximum relief amplitude (µm) D56 | +2% | 42% |
| Maximum relief amplitude (µm) D84 | −6% | 72% |

As demonstrated by the data shown in Table 1 above, there was a 5% decrease in the average roughness of 72% of test subjects' skin on day 84. A 5% decrease in the average height of skin wrinkles was observed in 69% of test subjects' skin on day 84. A 6% decrease in the maximum height of skin wrinkles was observed in 72% of test subjects' skin on day 84. The data demonstrate a significant smoothing and anti-wrinkle effect for a vast majority of users at the end of the test period by using the natural skincare composition according to Example 1.

The skin-firming effect of the composition was determined using an add-on to the DermaTOP® system known as DynaSKIN® and its attendant dedicated software. This system measures the skin-deformation parameters of volume, surface and depth associated with firmness and laxity of the skin and its sag. A decrease in the volume, surface and depth of skin deformation corresponds to an increase in skin firmness. The data pertaining to volume, surface, and maximum depth improvements after use of the composition according to Example 1 are presented in Table 2.

TABLE 2

| Parameters and Kinetics | Δ% on mean | % of subjects with the expected effect |
|---|---|---|
| Volume (mm³) D28 | −8% | 72% |
| Volume (mm³) D56 | −12% | 56% |
| Volume (mm³) D84 | −21% | 82% |
| Surface (mm²) D28 | −3% | 58% |
| Surface (mm²) D56 | −4% | 76% |
| Surface (mm²) D84 | −7% | 71% |
| Maximum depth (mm) D28 | −5% | 69% |
| Maximum depth (mm) D56 | −7% | 59% |
| Maximum depth (mm) D84 | −16% | 71% |

As demonstrated by the data in Table 2, use of the natural skincare composition according to Example 1 resulted in less voluminous and less extended deformation of test subjects' skin. The improvements to test subjects' skin firmness, laxity, and sag increased with time, with the vast majority experiencing significant reductions in skin deformation. For instance, over 70% of test subjects experienced a 21% decrease in volume, 7% decrease in surface, and 16% decrease in depth of deformation after 84 days of using the natural skincare composition.

Moisturization/hydration data was obtained using a Corneometer®, which measures capacitance of the skin, which corresponds to the humidity level of the measured skin. An increase in Corneometer® value corresponds therefore to a desired increase in moisturization/hydration. The data pertaining to skin-moisturization are presented below in Table 3.

TABLE 3

| Parameters and Kinetics | Δ% on mean | % of subjects with the expected effect |
|---|---|---|
| Cutaneous hydration rate D28 | 19% | 89% |
| Cutaneous hydration rate D56 | 36% | 94% |
| Cutaneous hydration rate D84 | 52% | 100% |

The data presented in Table 3 demonstrate the skin-moisturizing benefits of the natural skincare composition according to Example 1. Test subjects experienced a 19% increase in skin moisture after 28 days, a 36% increase after 56 days, and a 52% increase after 84 days, with 100% of test subjects experiencing the increase at 84 days.

The anti-aging effect of the composition was determined using a high-frequency echograph Dermascan® C 2D instrument which measures combined dermis and epidermis thickness. The device emits an ultrasound beam that generates a two-dimensional image of the dermis and epidermis used to measure the thickness of the skin. As a person ages, their skin naturally becomes thinner. Thus an increase in thickness between the epidermis and the dermo-hypodermis junction (which abuts the dermis) corresponds to a positive anti-aging effect. The data corresponding to the measurement are presented below in Table 4.

TABLE 4

| Parameters and Kinetics | Δ% on mean | % of subjects with the expected effect |
|---|---|---|
| Thickness of epidermis-dermis (mm) D28 | 3% | 64% |
| Thickness of epidermis-dermis (mm) D56 | 6% | 85% |
| Thickness of epidermis-dermis (mm) D84 | 6% | 85% |

As seen in Table 4 above, the natural skincare composition according to Example 1 has substantial anti-aging effects including a thicker epidermis-dermis after 28, 56, and 84 days of use, with 85% of test subjects showing a 6% increase in thickness after 84 days.

Another tool/data point used to determine skin health is SquameScan® software in conjunction with D-Squame® tape strips. This tool is designed to measure IR-light absorption and thereby determine stratum-corneum protein content on the D-Squame® strip. A decrease in light absorption corresponds to a decrease in the amount of protein detected, thus evidencing that the skin has experienced a desirable skin restructuring effect. The data from this measurement are provided below in Table 5.

TABLE 5

| Parameters and Kinetics | Δ% on mean | % of subjects with the expected effect |
|---|---|---|
| Light absorption (%) D28 | −5% | 47% |
| Light absorption (%) D56 | −13% | 59% |
| Light absorption (%) D84 | −19% | 76% |

As illustrated by the data in Table 5 above, statistically significant improvements to skin restructuring are observed in a majority of test subjects after 56 and 84 days, with a 13% and 19% decrease in UV absorption, respectively. The data demonstrate that the natural skincare composition according to Example 1 aids in skin restructuring effects.

The above-discussed in-vivo clinical testing clearly and quantitatively establishes, the significant impact on skin health and appearance achieved by the use the inventive composition of Example 1, with benefits such as smoother, less-wrinkled, firmer, more-moisturized, thicker, and restructured skin.

The test subjects were then asked to assess, qualitatively, their impression of the composition of Example 1 with respect to its sensorial qualities in general and its efficacy after 56 and 84 days of use. The test subjects all appreciated the sensorial qualities of the product with regards to its texture, color, ease of application, and non-greasy/non-sticky feel on their skin. With regards to their perception of the product's efficacy, they all believed that after 56, and especially 84 days of use their skin was more moisturized, nourished, comfortable, smooth, elastic, firm, dense, brightened/luminous, re-tightened, detoxified, healthy and more uniform in appearance.

Example 2

The efficacy of a skincare composition according to embodiments of the present disclosure and incorporated into different cosmetic products was measured against a leading cosmetic product. Five cosmetic products incorporating the skincare composition, including a face, hands, and body cream, an exfoliating wash, an eye gel cream, a day cream, and a facial oil, were measured against the leading cosmetic product, a day cream, using quantifiable metrics as described herein. Each of the users who participated in the study were instructed to wash their face for a one-week period using Cetaphil® Gentle Skin Cleanser prior to the study and to refrain from using any anti-aging treatments/products during the washout period and for the duration of the study.

The five cosmetic products incorporating the skincare composition according to embodiments of the disclosure and the leading cosmetic product were assessed using one or more quantifiable metrics such as a Corneometer® measurement, a Tewameter® measurement, Image Pro® software, a D-Squame® measurement, a Sebumeter® measurement, and a Cutometer® measurement.

As with Example 1, moisturization/hydration data was obtained using a Corneometer®, which measures capacitance of the skin, which corresponds to the humidity level of the measured skin. Since water is known to be an excellent conductor of electricity, an increase in electrical conductance corresponds to an increase in skin's hydration/moisture levels. An increase in Corneometer® value corresponds therefore to a desired increase in moisturization/hydration.

SquameScan® software was used in conjunction with D-Squame® tape strips to measure IR-light absorption and thereby determine stratum-corneum protein content on the D-Squame® strip. This measures the ability of the skin's outermost layer to effectively protect the body from external factors light sunlight and pollution, as well as retain moisture to prevent it from becoming dry, and is determined by the amount of particular skin proteins found in this layer. Specially designed tape is first applied onto the skin to remove dead skin cells from the surface, at which point the amount of protein in the cells is measured. A decrease in light absorption corresponds to a decrease in the amount of protein detected, thus evidencing that the skin has experienced a desirable skin restructuring effect.

Transepidermal water loss (TEWL) was evaluated using a Tewameter®, such as is available from Courage+Khazaka electronic GmbH of Köln, Germany, or alternatively by a VapoMeter from Delfin Technologies of Kuopio, Finland. This device measures skin's ability to retain water. When water passes through the skin, which is a natural biological process, and evaporates from the skin's surface, this phenomenon is referred to as TEWL and is a measure of skin's ability to retain moisture present in the dermis. If the skin's ability to retain moisture is enhanced after use of a product, its effectiveness as a moisturizer is confirmed.

Skin structure and dryness are measured using high-resolution images of the skin captured with a Visioscan®, also of Courage+Khazaka electronic GmbH.

Oil content on the skin was measured using a Sebumeter®, also of Courage+Khazaka electronic GmbH. The Sebumeter® evaluates the effectiveness of a product intended to reduce oil content on the skin by grease-spot photometry, in which the tape of the device contacts a user's skin and is then measured by a photocell.

Skin elasticity was measured using a Cutometer® available also from Courage+Khazaka electronic GmbH. The Cutometer® uses a suction method in which negative pressure mechanically deforms the skin. Skin is withdrawn into an aperture of a probe for a defined time, and measured using a non-contact optical measuring system. The resistance of the skin to the negative pressure represents firmness and its ability to return to its original position represents elasticity. Accordingly, a decrease in Cutometer® measurements indicates an improvement in skin firmness.

The face, hands, and body cream used in the study comprises (1) a preservative system comprising: (a) from about 2 to about 4% by weight, of a *Lactobacillus* ferment; (b) from about 2 to about 4% by weight, of a *Lactobacillus* and *Cocos nucifera* fruit extract; (c) from about 0.2 to about 0.4% by weight, of salicylic acid; (d) from about 0.2 to about 0.4% by weight, of at least one salt of a weak acid, preferably potassium sorbate; and (e) from about 4 to about 6% by weight, of a petroleum-free propanediol; (2) a moisturizing/hydrating-effective amount of a mixture of at least: (f) an oil infusion of *Calendula officinalis* having about 0.5% by weight of *Calendula officinalis* extract, and about 2% by weight of almond oil; (g) an oil infusion of *Helichrysum italicum* having about 1.2% by weight, of *Helichrysum italicum* extract, and about 4.7% by weight of almond oil; (h) an oil infusion of *Symphytum officinale* having about 0.5% by weight, of *Symphytum officinale* extract, and about 2% by weight of almond oil; (i) an aqueous infusion of *Viola tricolor* having about 2.5% by weight, of *Viola tricolor* extract; and (j) an aqueous infusion of at least one *Mallow* extract chosen from *Althea officinalis* and *Malva sylvestris* having about 2.5% by weight, of *Mallow* extract, wherein aqueous infusions (i) and (j) have a total water content of about 60% by weight; and a dermatologically acceptable emulsifier, and has a pH ranging from about 4.5 to about 5.5, preferably from about 4.8 to about 5.3. The combination of *Calendula officinalis, Helichrysum italicum, Symphytum officinale, Viola tricolor*, and at least one *Mallow* extract beneficially provides synergistic effects on the skin, including moisturizing the skin, protecting the skin with a film, shedding dry outer layers of the epidermis, improving osmotic function, and providing a soothing gel, as described above.

The exfoliating wash used in the study comprises a skincare composition comprises (1) a preservative system comprising (a) from about 2 to about 4% by weight, of a *Lactobacillus* ferment; (b) from about 2 to about 4% by weight, of a *Lactobacillus* and *Cocos nucifera* fruit extract; (c) from about 0.2 to about 0.4% by weight, of salicylic acid; (d) from about 0.2 to about 0.4% by weight, of at least one salt of a weak acid, preferably potassium sorbate; and (e) from about 4 to about 6% by weight, of a petroleum-free propanediol; (2) at least one of an Elderflower hydrosol; infusions of Milk Thistle oil; Castor oil; Safflower oil; Grapefruit essential oil; and jojoba beads; and (3) a dermatologically acceptable emulsifier, and has a pH ranging from about 4.5 to about 5.5, preferably from about 4.8 to about 5.3. This combination of ingredients advantageously provides synergistic effects that gently tone the skin, provide antioxidants, reduce pore size while cleaning and hydrating, provide uplifting scents, and lightly exfoliate the skin without irritation.

The eye gel cream used in the study comprises a skincare composition comprises (1) a preservative system comprising (a) from about 2 to about 4% by weight, of a *Lactobacillus* ferment; (b) from about 2 to about 4% by weight, of a *Lactobacillus* and *Cocos nucifera* fruit extract; (c) from about 0.2 to about 0.4% by weight, of salicylic acid; (d) from about 0.2 to about 0.4% by weight, of at least one salt of a weak acid, preferably potassium sorbate; and (e) from about 4 to about 6% by weight, of a petroleum-free propanediol; (2) at least one of *Helichrysum italicum*; cucumber; aloe vera; and infusions of Arnica oil and Bladder Wrack oil; and (3) a dermatologically acceptable emulsifier, and has a pH ranging from about 4.5 to about 5.5, preferably from about 4.8 to about 5.3. This combination of ingredients advantageously reduces puffiness around the eyes, reduces irritation and moisture loss, hydrates the skin by providing a moisture-retentive film, provides amino acids, proteins and lipids that plump and calm the skin, and soothes and hydrates the skin while increasing firmness.

The day cream used in the study comprises a skincare composition comprises (1) a preservative system comprising (a) from about 2 to about 4% by weight, of a *Lactobacillus* ferment; (b) from about 2 to about 4% by weight, of a *Lactobacillus* and *Cocos nucifera* fruit extract; (c) from about 0.2 to about 0.4% by weight, of salicylic acid; (d) from about 0.2 to about 0.4% by weight, of at least one salt of a weak acid, preferably potassium sorbate; and (e) from about 4 to about 6% by weight, of a petroleum-free propanediol; (2) at least one of *Calendula*-infused oil and water; Serrated Wrack; Hyaluronic acid from about 1 to about 3% by weight; Sweet Almond oil; and Green Mandarin oil; and (3) a dermatologically acceptable emulsifier, and has a pH ranging from about 4.5 to about 5.5, preferably from about 4.8 to about 5.3. This combination of ingredients advantageously improves skin distensibility, firmness, and viscoelasticity, improves skin suppleness and elasticity by moisturizing and improving the skin barrier, boosts the skin's ability to absorb moisture resulting in smoother, softer skin, and tones and balances oil production of the skin.

The facial oil used in the study comprises a skincare composition comprises (1) a preservative system comprising (a) from about 2 to about 4% by weight, of a *Lactobacillus* ferment; (b) from about 2 to about 4% by weight, of a *Lactobacillus* and *Cocos nucifera* fruit extract; (c) from about 0.2 to about 0.4% by weight, of salicylic acid; (d) from about 0.2 to about 0.4% by weight, of at least one salt of a weak acid, preferably potassium sorbate; and (e) from about 4 to about 6% by weight, of a petroleum-free propanediol; (2) at least one of Rosehip oil; Bog Myrtle; Sea Buckthorn; Prickly Pear Seed oil; Serrated Wrack; Rosemary; Kiwi Seed oil; and Baobab oil; and (3) a dermatologically acceptable emulsifier, and has a pH ranging from about 4.5 to about 5.5, preferably from about 4.8 to about 5.3. This combination of ingredients advantageously smoothes, moisturizes, and softens the skin, providing vitamins A, C, D, E, and K and essential fatty acids, cleans the pores, provides antioxidants, retains moisture and improves skin elasticity and suppleness, reduces hyperpigmentation, protects the skin from environmental stressors, controls sebum production, and maintains clear skin.

It will be understood that the above cosmetic products and listed ingredients are merely exemplary and may further comprise any necessary components such as emulsifiers, fragrances, natural preservatives, and other ingredients within any suitable proportion.

It has been surprisingly found that the five cosmetic products incorporating the skincare compositions described above achieve enhanced skincare relative to the leading dermatological product as well as compared to baseline skin health across numerous quantifiable metrics as described in greater detail below. The leading dermatological product used as a benchmark is a moisturizing cream comprising conventional dermatological ingredients, as well as hyaluronic acid, dimethicone, and ceramides.

Users' skin was first measured using a Corneometer® as described above to assess skin hydration and compared against a control group using the leading dermatological product. Measurements were taken at the outset of the study to establish a baseline measurement, after 14 days, and after 28 days. The results are shown below in Table 6, in which a positive value represents an improvement in skin hydration.

TABLE 6

| | Day 14 | | Day 28 | |
| --- | --- | --- | --- | --- |
| | % Change from Baseline | % Subjects | % Change from Baseline | % Subjects |
| Leading Dermatological Product | 77.4 | 100 | 90.2 | 100 |
| Face, hands, and body cream | 22.1 | 83 | 42.5 | 90 |
| Day Cream | 52 | 100 | 50.1 | 100 |
| Facial Oil | 133.7 | 100 | 168.2 | 100 |
| Eye Gel Cream | 86.9 | 100 | 70.1 | 100 |

As shown from the results of Table 6 above, the skincare compositions according to the disclosure universally achieve an improvement in skin hydration for all or a large majority of users, with the facial oil comprising the skincare composition achieving an especially marked improvement relative to baseline hydration and relative to the leading dermatological product.

Users' skin was also measured to assess skin barrier function—as indicated by transepidermal water loss (TEWL)—using a Tewameter® as described above. Measurements were taken at the outset of the study to establish a baseline measurement, after 14 days, and after 28 days. The results are shown below in Table 7, in which a negative value represents an improvement in skin barrier function.

TABLE 7

| | Day 14 | | Day 28 | |
| --- | --- | --- | --- | --- |
| | % Change from Baseline | % Subjects | % Change from Baseline | % Subjects |
| Leading Dermatological Product | −1.9 | 59 | −5.0 | 63 |
| Face, hands, and body cream | −7.0 | 57 | −13.4 | 77 |
| Day Cream | 0.9 | 47 | −4.5 | 50 |
| Facial Oil | −6.5 | 83 | −11.2 | 83 |
| Exfoliating Wash | −13.1 | 81 | −14.0 | 74 |

As seen from the results in Table 7, the skincare compositions of the disclosure as embodied in four of the five skincare products achieve universally an improvement in skin barrier function relative to baseline by day 28, and with the exception of the Day Cream product achieve a larger improvement for a larger percentage of users than the leading dermatological product.

Users' skin was also measured to assess skin texture using image analysis. At each evaluation, digital images of the face of each user were taken from the front, right, and left. The images were analyzed using Image Pro® software of MediaCybernetics of Bethesda, Md., to determine changes to the following parameters: skin texture/smoothness, under eye puffiness, and under eye discoloration.

Visia CR® was used to generate a texture score for the skin based on the mean intensities of the red, green, and blue pixels of the captured images. A decrease in the texture score calculated according to this method represents an improvement in overall skin texture. Under-eye puffiness is determined in a similar manner.

Under-eye discoloration was measured by assessing chroma. The degree to which a color is free from being mixed with other colors indicates its chromaticity. An increase in chromaticity represents an improvement in under-eye discoloration.

Measurements were taken at the outset of the study to establish a baseline measurement, after 14 days, and after 28 days. The results of the skin-texture assessment are shown below in Table 8, in which a negative value represents an improvement in skin texture.

TABLE 8

|  | Day 14 | | Day 28 | |
| --- | --- | --- | --- | --- |
|  | % Change from Baseline | % Subjects | % Change from Baseline | % Subjects |
| Leading Dermatological Product | 4.8 | 19 | −1.9 | 81 |
| Face, hands, and body cream | 1.1 | 45 | −2.2 | 80 |
| Day Cream | 1.5 | 47 | −5.1 | 77 |
| Facial Oil | −1.7 | 60 | −5.2 | 77 |

As seen in Table 8 above, the use of skincare compositions according to the disclosure advantageously improves skin texture relative to the leading dermatological product, and in most cases for a larger number of users.

Results for under-eye puffiness and discoloration assessed using the Image Pro® method described above are shown in Tables 9 and 10 below, in which a negative value and a positive value, respectively, represent an improvement.

TABLE 9

|  | Day 14 | | Day 28 | |
| --- | --- | --- | --- | --- |
|  | % Change from Baseline | % Subjects | % Change from Baseline | % Subjects |
| Leading Dermatological Product | 2.6 | 38 | −2.1 | 78 |
| Eye gel cream | −0.7 | 71 | −0.6 | 71 |

As seen from the results shown in Table 9 above, the use of skincare compositions according to the present disclosure advantageously improve a user's under-eye puffiness, particularly after 14 days, in which period the improvement is more substantial and observed over a larger percentage of users than for the leading dermatological product.

TABLE 10

|  | Day 14 | | Day 28 | |
| --- | --- | --- | --- | --- |
|  | % Change from Baseline | % Subjects | % Change from Baseline | % Subjects |
| Leading Dermatological Product | −0.03 | 56 | 0.31 | 47 |
| Eye gel cream | 0.3 | 52 | 1.7 | 77 |

As seen from the results in Table 10 above, the use of skincare compositions according to the present disclosure advantageously improve a user's under-eye discoloration compared to the leading dermatological product and for a larger percentage of users.

A Sebumeter® was used to measure facial sebum/oil levels of users using the leading dermatological product, the facial oil, and the exfoliating wash. The results are shown in Table 11 below, wherein a negative value represents an improvement.

TABLE 11

|  | Day 14 | | Day 28 | |
| --- | --- | --- | --- | --- |
|  | % Change from Baseline | % Subjects | % Change from Baseline | % Subjects |
| Leading Dermatological Product | −15.0 | 75 | −19.2 | 81 |
| Facial oil | −22.5 | 90 | −27.5 | 93 |
| Exfoliating wash | −5.5 | 55 | 4.2 | 39 |

As seen from the results in Table 11 above, the skincare compositions according to the disclosure advantageously improve a user's facial sebum/oil levels compared to baseline and to a greater degree and for a greater percentage of users than the leading dermatological product, particularly when used in the facial oil product.

Users' skin flakiness was compared using D-Squame® as described above and assessed across the leading dermatological product, the face, hands, and body cream, the day cream, the facial oil, and the exfoliating wash products. The results of the D-Squame® measurements are shown in Table 12 below, in which a negative value represents an improvement in skin flakiness.

TABLE 12

|  | Day 14 | | Day 28 | |
| --- | --- | --- | --- | --- |
|  | % Change from Baseline | % Subjects | % Change from Baseline | % Subjects |
| Leading Dermatological Product | −26.4 | 84 | −41.2 | 100 |
| Face, hands, and body cream | −21.6 | 73 | −40.5 | 100 |
| Day Cream | −33 | 93 | −50 | 100 |
| Facial Oil | −28.6 | 100 | −42.9 | 100 |
| Exfoliating Wash | −26.5 | 74 | −47.1 | 100 |

As seen from the results in Table 12 above, the skincare compositions of the disclosure advantageously improve universally skin flakiness relative to baseline, and certain of the disclosed embodiments show greater improvement for a higher percentage of users than the leading dermatological product.

The users' skin firmness was also measured using a Cutometer® and assessed for both the leading dermatological product and the facial oil product, the results of which are shown in Table 13 below. A negative value indicates an improvement to skin firmness.

TABLE 13

|  | Day 14 | | Day 28 | |
| --- | --- | --- | --- | --- |
|  | % Change from Baseline | % Subjects | % Change from Baseline | % Subjects |
| Leading Dermatological Product | −29.0 | 69 | −47.3 | 75 |
| Facial oil | −21.8 | 73 | −24.4 | 30 |

As seen from the results of Table 13 above, the use of skincare compositions according to the disclosure advantageously improves a user's skin firmness relative to baseline.

By providing a skincare composition and method for using the same according to embodiments of the disclosure, the problem of existing cosmetics such as moisturizers using harmful synthetic and/or petroleum-based ingredients, and the problem of "all-natural" cosmetics lacking credible and/or rigorous demonstrations of their efficacy and benefits, is addressed. The composition comprising a combination of natural botanical ingredients such as *Calendula officinalis, Helichrysum italicum, Symphytum officinale, Viola tricolor*, and *Mallow* moisturizes, soothes, and nourishes the skin by providing a protective film and gel on the skin, helping the skin shed the dry outer layers of the epidermis and by improving osmotic function to better retain water while avoiding the undesirable complications of synthetic and/or petroleum-based moisturizers. The compositions may further be combined with an all-natural preservative system that improves the chemical stability and shelf-life of the composition without using harsh, irritating synthetic preservatives.

The skilled artisan will recognize the interchangeability of various components and ingredients from the embodiments described. Besides the variations described, other known equivalents for each feature can be mixed and matched by one of ordinary skill in this art to prepare a skincare composition under principles of the present disclosure. Therefore, the embodiments described may be adapted to compositions for any purpose and utilizing any suitable ingredient.

While the foregoing embodiments have been described, it is understood that alternatives and modifications of these embodiments, such as those suggested by others, may be made to fall within the scope of the disclosure.

What is claimed is:

1. A composition for application onto human skin comprising:
    (1) a moisturizing/hydrating-effective amount of a mixture of at least:
        (a) a vegetable oil infusion of *Calendula officinalis* extract;
        (b) a vegetable oil infusion of *Helichrysum italicum* extract;
        (c) a vegetable oil infusion of *Symphytum officinale* extract;
        (d) an aqueous infusion of *Viola tricolor* extract; and
        (e) an aqueous infusion of at least one *Mallow* extract chosen from *Malva sylvestris* extract and *Althea officinalis* extract;
    (2) an emulsifying-effective amount of a dermatologically-acceptable emulsifier; and
    (3) a dermatologically acceptable carrier, wherein the composition is natural and free of a skin sensitizing-effective amount of an essential oil.

2. The composition of claim 1, wherein (a) contains from about 0.3 to about 0.6% by weight, of *Calendula officinalis* extract and from about 1 to about 3% by weight of a vegetable oil,
    wherein (b) contains from about 0.9 to about 1.3% by weight of *Helichrysum italicum* extract and from about 4 to about 7% by weight of a vegetable oil,
    wherein (c) contains from about 0.3 to about 0.6% by weight of *Symphytum officinale* extract and from about 1 to about 3% by weight of a vegetable oil,
    wherein (d) contains from about 2 to about 3% by weight of *Viola tricolor* extract,
    wherein (e) contains from about 2 to about 3% by weight of *Althea officinalis* extract, and
    wherein aqueous infusions (d) and (e) have a total water content of from about 50 to about 70% by weight, all weights based on the total weight of the composition.

3. The composition of claim 1, wherein (a) contains about 0.5% by weight of *Calendula officinalis* extract and about 2% by weight of almond oil,
    wherein (b) contains about 1.2% by weight of *Helichrysum italicum* extract and about 4.7% by weight of almond oil,
    wherein (c) contains about 0.5% by weight of *Symphytum officinale* extract and about 2% by weight of almond oil,
    wherein (d) contains about 2.5% by weight of *Viola tricolor* extract,
    wherein (e) contains about 2.5% by weight of *Althea officinalis* extract, and
    wherein (d) and (e) have a total water content of about 60% by weight, all weights based on the total weight of the composition.

4. The composition of claim 1, wherein the vegetable oil is almond oil.

5. The composition of claim 1, wherein the composition is in at least one form chosen from a solution, suspension, lotion, cream, gel, spray, ointment, or serum.

6. A composition for application onto human skin comprising:
    (1) an effective amount of a preservative system containing:
        (a) from about 1 to about 5% by weight of a *Lactobacillus* ferment;
        (b) from about 1 to about 5% by weight, of a *Cocos nucifera* fruit extract fermented and/or included with *Lactobacillus;*
        (c) up to 0.5% by weight of salicylic acid;
        (d) from about 0.1 to about 0.5% by weight of at least one salt of a weak acid; and
        (e) from about 1 to about 10% by weight of a petroleum-free propanediol;
    (2) a moisturizing/hydrating-effective amount of a mixture of at least:
        (f) a vegetable oil infusion of *Calendula officinalis* extract;
        (g) a vegetable oil infusion of *Helichrysum italicum* extract;
        (h) a vegetable oil infusion of *Symphytum officinale* extract;
        (i) an aqueous infusion of *Viola tricolor* extract; and
        (j) an aqueous infusion of at least one *Mallow* extract chosen from *Malva sylvestris* extract and *Althea officinalis* extract;
    (3) an emulsifying-effective amount of a dermatologically acceptable emulsifier; and
    (4) a dermatologically acceptable carrier, wherein the composition is natural, free of a skin-sensitizing-effective amount of an essential oil and has a pH ranging from about 4.5 to about 5.5.

7. The composition of claim 6, wherein (a) is employed in an amount of from about 2 to about 4% by weight,
    wherein (b) is employed in an amount of from about 2 to about 4% by weight,
    wherein (c) is employed in an amount of from about 0.1 to about 0.45% by weight,
    wherein (d) is employed in an amount of from about 0.2 to about 0.4% by weight, and
    wherein (e) is employed in an amount of from about 2 to about 8% by weight, all weights based on the total weight of the composition.

8. The composition of claim 6, wherein (a) is employed in an amount of from about 2 to about 4% by weight, wherein (b) is employed in an amount of from about 2 to about 4% by weight, wherein (c) is employed in an amount of from about 0.1 to about 0.45% by weight, wherein (d) is employed in an amount of from about 0.2 to about 0.4% by weight, and wherein (e) is employed in an amount of from about 2 to about 8% by weight, all weights based on the total weight of the composition.

9. The composition of claim 6, wherein (f) contains from about 0.3 to about 0.6% by weight, of *Calendula officinalis* extract and from about 1 to about 3% by weight of a vegetable oil, wherein (g) contains from about 0.9 to about 1.3% by weight of *Helichrysum italicum* extract and from about 4 to about 7% by weight of a vegetable oil, wherein (h) contains from about 0.3 to about 0.6% by weight of *Symphytum officinale* extract and from about 1 to about 3% by weight of a vegetable oil, wherein (i) contains from about 2 to about 3% by weight of *Viola tricolor* extract, wherein (j) contains from about 2 to about 3% by weight of *Althea officinalis* extract, and wherein aqueous infusions (d) and (e) have a total water content of from about 50 to about 70% by weight, all weights based on the total weight of the composition.

10. The composition of claim 6, wherein (f) contains about 0.5% by weight of *Calendula officinalis* extract and about 2% by weight of almond oil, wherein (g) contains about 1.2% by weight of *Helichrysum italicum* extract and about 4.7% by weight of almond oil, wherein (h) contains about 0.5% by weight of *Symphytum officinale* extract and about 2% by weight of almond oil, wherein (i) contains about 2.5% by weight of *Viola tricolor* extract, wherein (j) contains about 2.5% by weight of *Althea officinalis* extract, and wherein (d) and (e) have a total water content of about 60% by weight, all weights based on the total weight of the composition.

11. The composition of claim 6 having a pH of from about 4.8 to about 5.3.

12. The composition of claim 6, wherein the vegetable oil is almond oil.

13. A method of enhancing skin health and appearance comprising applying onto the skin an effective amount of a composition containing:

(1) a moisturizing/hydrating-effective amount of a mixture of at least:
  (a) a vegetable oil infusion of *Calendula officinalis* extract;
  (b) a vegetable oil infusion of *Helichrysum italicum* extract;
  (c) a vegetable oil infusion of *Symphytum officinale* extract;
  (d) an aqueous infusion of *Viola tricolor* extract; and
  (e) an aqueous infusion of at least one *Mallow* extract chosen from *Malva sylvestris* extract and *Althea officinalis* extract;

(2) an emulsifying-effective amount of a dermatologically-acceptable emulsifier; and (3) a dermatologically acceptable carrier, wherein the composition is natural and free of a skin sensitizing-effective amount of an essential oil.

14. The method of claim 13, wherein (a) contains from about 0.3 to about 0.6% by weight, of *Calendula officinalis* extract and from about 1 to about 3% by weight of a vegetable oil, wherein (b) contains from 0.9 to about 1.3% by weight of *Helichrysum italicum* extract and from about 4 to about 7% by weight of a vegetable oil, wherein (c) contains from about 0.3 to about 0.6% by weight of *Symphytum officinale* extract and from about 1 to about 3% by weight of a vegetable oil, wherein (d) contains from about 2 to about 3% by weight of *Viola tricolor* extract, wherein (e) contains from about 2 to about 3% by weight of *Althea officinalis* extract, and wherein aqueous infusions (d) and (e) have a total water content of from about 50 to about 70% by weight, all weights based on the total weight of the composition.

15. The method of claim 13, wherein (a) contains about 0.5% by weight of *Calendula officinalis* extract and about 2% by weight of almond oil, wherein (b) contains about 1.2% by weight of *Helichrysum italicum* extract and about 4.7% by weight of almond oil, wherein (c) contains about 0.5% by weight of *Symphytum officinale* extract and about 2% by weight of almond oil, wherein (d) contains about 2.5% by weight of *Viola tricolor* extract, wherein (e) contains about 2.5% by weight of *Althea officinalis* extract, and wherein (d) and (e) have a total water content of about 60% by weight, all weights based on the total weight of the composition.

16. The method of claim 13, wherein the vegetable oil is almond oil.

17. The method of claim 13, wherein the composition is in at least one form chosen from a solution, suspension, lotion, cream, gel, spray, ointment or serum.

18. A method of enhancing skin health and appearance comprising applying onto the skin an effective amount of a composition containing:

(1) a preservative system having:
  (a) from about 1 to about 5% by weight of a *Lactobacillus* ferment;
  (b) from about 1 to about 5% by weight, of a *Cocos nucifera* fruit extract fermented and/or included with *Lactobacillus*;
  (c) up to 0.5% by weight of salicylic acid;
  (d) from about 0.1 to about 0.5% by weight of at least one salt of a weak acid; and
  (e) from about 1 to about 10% by weight of a petroleum-free propanediol;

(2) a moisturizing/hydrating-effective amount of a mixture of at least:
  (f) a vegetable oil infusion of *Calendula officinalis* extract;
  (g) a vegetable oil infusion of *Helichrysum italicum* extract;
  (h) a vegetable oil infusion of *Symphytum officinale* extract;
  (i) an aqueous infusion of *Viola tricolor* extract; and
  (j) an aqueous infusion of at least one *Mallow* extract chosen from *Malva sylvestris* extract and *Althea officinalis* extract;

(3) an emulsifying-effective amount of a dermatologically acceptable emulsifier; and (4) a dermatologically acceptable carrier, wherein the composition is natural, free of a skin-sensitizing-effective amount of an essential oil and has a pH ranging from about 4.5 to about 5.5.

19. The method of claim 18, wherein (a) is employed in an amount of from about 2 to about 4% by weight,
wherein (b) is employed in an amount of from about 2 to about 4% by weight,
wherein (c) is employed in an amount of from about 0.1 to about 0.45% by weight,
wherein (d) is employed in an amount of from about 0.2 to about 0.4% by weight, and
wherein (e) is employed in an amount of from about 2 to about 8% by weight, all weights based on the total weight of the composition.

20. The method of claim 18, wherein (f) contains from about 0.3 to about 0.6% by weight, of *Calendula officinalis* extract and from about 1 to about 3% by weight of a vegetable oil,
wherein (g) contains from about 0.9 to about 1.3% by weight of *Helichrysum italicum* extract and from about 4 to about 7% by weight of a vegetable oil,
wherein (h) contains from about 0.3 to about 0.6% by weight of *Symphytum officinale* extract and from about 1 to about 3% by weight of a vegetable oil,
wherein (i) contains from about 2 to about 3% by weight of *Viola tricolor* extract,
wherein (j) contains from about 2 to about 3% by weight of *Althea officinalis* extract, and
wherein aqueous infusions (d) and (e) have a total water content of from about 50 to about 70% by weight, all weights based on the total weight of the composition.

21. The method of claim 18, wherein (f) contains about 0.5% by weight of *Calendula officinalis* extract and about 2% by weight of almond oil,
wherein (g) contains about 1.2% by weight of *Helichrysum italicum* extract and about 4.7% by weight of almond oil,
wherein (h) contains about 0.5% by weight of *Symphytum officinale* extract and about 2% by weight of almond oil,
wherein (i) contains about 2.5% by weight of *Viola tricolor* extract,
wherein (j) contains about 2.5% by weight of *Althea officinalis* extract, and
wherein (d) and (e) have a total water content of about 60% by weight, all weights based on the total weight of the composition.

22. The method of claim 18, wherein the vegetable oil is almond oil.

23. The method of claim 18, wherein the composition is in at least one form chosen from a solution, suspension, lotion, cream, gel, spray, ointment, or serum.

24. The method of claim 18, wherein (a) is employed in an amount of from about 2 to about 4% by weight,
wherein (b) is employed in an amount of from about 2 to about 4% by weight,
wherein (c) is employed in an amount of from about 0.2 to about 0.45% by weight,
wherein (d) is employed in an amount of from about 0.2 to about 0.4% by weight, and
wherein (e) is employed in an amount of from about 2 to about 8% by weight, all weights based on the total weight of the composition.

25. The method of claim 18, wherein the composition has a pH of from about 4.8 to about 5.3.

* * * * *